United States Patent [19]

Murata

[11] 4,405,560

[45] Sep. 20, 1983

[54] CARRIER FOR HOLDING ANALYTICAL SAMPLES

[75] Inventor: Michihiro Murata, Kyoto, Japan

[73] Assignee: Murata Manufacturing Co., Ltd., Nagaokakyo, Japan

[21] Appl. No.: 309,473

[22] Filed: Oct. 7, 1981

[51] Int. Cl.³ .......................... B01L 3/00; G01N 1/28
[52] U.S. Cl. ..................................... 422/102; 422/58; 422/68; 435/805; 436/172
[58] Field of Search .............. 435/805, 299, 300, 301; 422/56, 58, 66, 68, 104, 99; 23/230 R; 250/272; 356/244, 428

[56] References Cited

U.S. PATENT DOCUMENTS

| | | | |
|---|---|---|---|
| 2,129,754 | 9/1938 | Yogoda | 422/56 |
| 2,771,398 | 11/1956 | Snyder | 435/805 |
| 3,923,463 | 12/1975 | Bagshaw et al. | 422/66 |
| 4,087,326 | 5/1978 | Kereluk | 435/805 |
| 4,340,565 | 7/1982 | Kitajima et al. | 422/55 |

*Primary Examiner*—Michael S. Marcus
*Attorney, Agent, or Firm*—Birch, Stewart, Kolasch and Birch

[57] ABSTRACT

A carrier which is used when a solution, as an analytical sample, is analyzed by X-ray fluorometry. The carrier is formed in its central region with a plurality of alternate slits and support connections, support connection each defined between adjacent slits. The configuration defines an island-like portion contrasted with the surrounding region and serving to hold the analytical solution, with the presence of the slits preventing the analytical solution from permeating into the surrounding region. The island-like portion is formed with a plurality of preformed fine holes.

5 Claims, 3 Drawing Figures

CARRIER FOR HOLDING ANALYTICAL SAMPLES

BACKGROUND OF THE INVENTION

1. Field of the Invention

The present invention relates to a carrier for holding analytical samples which is used when a solution is analyzed by X-ray fluorometry.

2. Description of the Prior Art

Where a trace amount of solution is to be analyzed by X-ray fluorometry, it has been common practice to allow the solution to permeate into a carrier, such as filter paper, and dry it to provide for X-ray analysis.

FIG. 1 is a plan view showing a conventional example of such a carrier. As shown in FIG. 1, the filter paper 1 has not been given any special treatment, with the result that when a solution is allowed to permeate, it diffuses throughout the filter paper 1. Moreover, since it diffuses ununiformly, it has been impossible to ensure that the diameter of a spot 2 of the solution is constant. As a result, large variations in the X-ray intensity being observed are produced, making accurate measurement impossible.

SUMMARY OF THE INVENTION

In brief, the present invention provides a carrier for holding analytical samples, wherein in order to limit a portion serving as a region for holding analytical samples to a fixed range, an island-like portion contrasted with the surrounding region is defined by an annular boundary zone comprising a plurality of alternate slits and support portions, each support portion defined between adjacent slits. According to the invention, the presence of the slits contributes to establishing a state in which the solution, as an analytical sample, is held in the island-like portion without permeating into the surrounding region. Therefore, accurate X-ray fluorometry can be effected. Further, according to the invention, the island-like portion is formed with a plurality of fine holes. More particularly, during analysis, X-rays strike the island-like portion and the reflection of the X-rays from said portion determines the background intensity. Therefore, if preformed fine holes are formed, the X-ray reflection is reduced by an amount corresponding to the total area of the fine holes, so that, in X-ray fluorometry, the background intensity is correspondingly lowered. As a result, the lower limit of quantitative analysis is greatly lowered, thus enabling the analysis of infinitesimal amounts of samples.

According to a preferred embodiment of the invention, the support portions are subjected to a solution diffusion preventive treatment, which more perfectly inhibits the solution from permeating into the surrounding region.

Accordingly, a principal object of the invention is to provide a carrier capable of holding a sample in a fixed region with high reproducibility.

Another object of the invention is to provide a carrier capable of greatly lowering the lower limit of quantitative limiting concentration.

The above and other objects and features of the invention will become more apparent from the following detailed description to be given with reference to the accompanying drawing.

DESCRIPTION OF THE PREFERRED EMBODIMENTS

Figure 2:
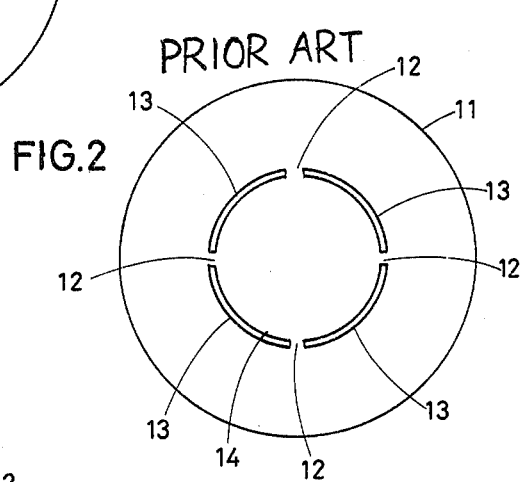
FIG. 2 is a plan view showing a prior art example relevant to the invention.

FIG. 2 shows a prior art example of interest to the invention. This prior art carrier was invented by the same inventor as the present invention and is disclosed in Japanese Utility Model Laying Open No. 125293/1979, laid open on Sept. 1, 1979 for public inspection.

Referring to FIG. 2, the main body 11 of a carrier is made of filter paper, membrane filter or synthetic filter made of polypropylene, cellulose ester or the like. The main body 11 has an island-like portion 14 defined therein by arcuate slits 13 cut therein leaving support portions 12 as connections.

A concrete example of this prior art carrier is given below.

Filter paper in the form of a disc of 40 mm in diameter was formed with 1-mm wide, 10-mm radius arcuate slits leaving 1-mm wide support portions at 4 places. The support portions were impregnated with paraffin to prevent the sample solution from permeating from the island-like portion defined by the slits into the other region. Subsequently, 60 µl of a standard copper solution (1 mg/1 ml) was dropwise added to the island-like portion to permeate through the latter. The carrier was then dried with air and the CuKα line X-ray intensity was measured.

For comparison purposes, filter paper of the same size but not having the above described treatment applied thereto was prepared and 60 µl of the same standard copper solution as described above was dropwise applied to the central region of the filter paper to permeate through the latter. The CuKα line X-ray intensity was measured.

The following table shows the results of measurements of the CuKα line intensities of the two samples and their standard deviations.

| Sample | CuKα line intensity (cps) | Standard Deviation (cps) |
| --- | --- | --- |
| This Example (FIG. 2) | 13,450 | 18.3 |
| Conventional Example (FIG. 1) | 5,847 | 155 |

When the two shown above were compared, it was found that in the conventional example since the region carrying the sample changed in shape for each sample, the CuKα line intensity was low and its variations were large.

On the other hand, according to this prior art example, the sample can be carried exclusively on the island-like portion, so that the CuKα line intensity is high and its variations are small.

Figure 1:
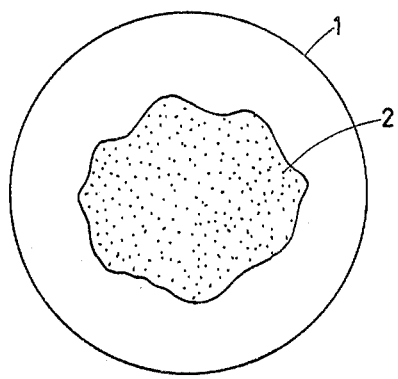
FIG. 1 is a plan view showing a conventional example of a carrier.

According to the prior art described above, the accuracy of X-ray fluorometry can be improved but the lower limit of quantitative limiting concentration can not be lowered. The reason is that the reflection of the X-rays from the island-like portion 14 is substantially the same as the central region of the filter paper 1 as shown in FIG. 1. More particularly, during analysis, X-rays strike the central region or the portion 14 and the reflection of the X-rays from the portion 14 determines the background intensity. Therefore, the lower limit of quantitative limiting concentration can not be lowered as a result of the background intensity.

Figure 3:
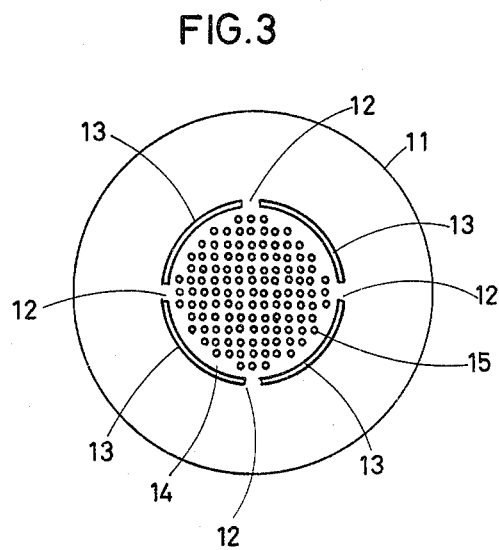
FIG. 3 is a plan view showing an embodiment of the invention.

Referring to FIG. 3, which shows an embodiment of the invention, the island-like portion 14 is formed with a plurality of fine holes 15 distributed thereover. Since the rest of the arrangement is the same as in the carrier shown in FIG. 2, the corresponding parts are given like reference numerals and the description of the corresponding parts is the same as the description given previously with reference to FIG. 2.

A concrete example of the embodiment shown in FIG. 3 is given below.

Paper filter having a diameter of 40 mm was formed with 1-mm wide, 10-mm radius arcuate slits leaving 1-mm wide support portions at 4 places. Further, the inner island-like portion was formed with a number of preformed fine holes of 1 mm in diameter such that the total area of the fine holes was 40% of the area of the island-like portion.

The support portions were impregnated with paraffin to prevent the sample solution from permeating from the island-like portion defined by the slits into the other region.

In order to compare the carrier thus obtained with the carrier obtained in the example shown in FIG. 2, these two subjects were tested for background intensity by X-ray fluorometry; a decrease of 10–30% in background intensity was attained by the provision of the fine holes. For example, whereas in FeK$\alpha$ line measurements the quantitative lower limit was 80 ng where fine holes were not provided, a quantitative lower limit of 48 ng was attained by providing fine holes. The quantitative lower limit was successfully lowered to $\frac{1}{2}$–$\frac{1}{3}$ of the conventional value, depending upon elements to be measured.

In addition, while the total area of the fine holes has been described as being 40% of the area of the island-like portion, it is not limited to this value. For example, it is preferable to set it in the range of 10–70%.

In the above embodiment, the support portions have been subjected to a solution diffusion preventive treatment with paraffin, but besides this, wax, collodion, cellulose ester or the like dissolved in a solvent may be used with which to impregnate the support portions to prevent diffusion of the solution, the idea being to use any suitable material that is capable of preventing diffusion of a medium which converts a sample into a solution.

In addition, where there is no need to pay so much attention to the diffusion of the solution, the support portions may not be subjected to such a solution diffusion preventive treatment.

Further, in the above embodiment the support portions have been provided at 4 places, but they may be provided at 2 or 3 places, the idea being to hold the island-like portion in the main body of the carrier, there being no limitation in the number thereof. In addition, it is preferable to prevent the island-like portion from bending after drying the carrier in which the sample solution permeates into the island-like portion, because the bending of the island-like portion may cause variations in the results of measurements. Therefore, the support portions are preferably provided at 3 or more places.

Further, the shape of the island-like portion is not limited to a circle; other shapes may be used as desired.

The shape and width of the slits are also optional.

Further, the thinner the carrier is, the better, because the background intensity is correspondingly lowered according to a decrease of the thickness of the carrier and, therefore, the lower limit of quantitative analysis can be lowered. It was found that, for example, the favorable results of analysis can be obtained by the carrier of the order of 200 $\mu$m in thickness.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A carrier comprising a medium for holding analytical samples to be subjected to X-ray analysis and having a natural porosity such that solutions of said samples are allowed to permeate into said medium by means of capillary action, comprising an island-like portion to hold said analytical samples contrasted with the surrounding region and defined by a plurality of alternate slits and support portions, each support portion defined between adjacent slits, said island-like portion being formed with a plurality of fine preformed holes, each hole having a diameter of about 1 mm, which comprise 10–70% of the area of the island-like portion.

2. A carrier as set forth in claim 1, wherein the support portions are subjected to a solution diffusion preventive treatment.

3. A carrier as set forth in claim 2, wherein said preventive solution comprises paraffin.

4. A carrier as set forth in claim 1, wherein the shape of said island-like portion is defined by a circle, and said support portions are distributed at regular intervals.

5. A carrier as set forth in claim 4, wherein said support portions number at least three.

* * * * *